(12) United States Patent
Kirchmair

(10) Patent No.: US 12,181,092 B2
(45) Date of Patent: Dec. 31, 2024

(54) STERILE CONNECTOR

(71) Applicant: Single Use Support GmbH, Kufstein (AT)

(72) Inventor: Johannes Kirchmair, Brandenberg (AT)

(73) Assignee: SINGLE USE SUPPORT GmbH, Kufstein (AT)

( * ) Notice: Subject to any disclaimer, the term of this patent is extended or adjusted under 35 U.S.C. 154(b) by 218 days.

(21) Appl. No.: 17/399,350

(22) Filed: Aug. 11, 2021

(65) Prior Publication Data
US 2022/0057035 A1 Feb. 24, 2022

(30) Foreign Application Priority Data
Aug. 18, 2020 (EP) .................................... 20191552

(51) Int. Cl.
*F16L 37/26* (2006.01)
*F16J 15/06* (2006.01)
*A61M 39/18* (2006.01)

(52) U.S. Cl.
CPC ............. *F16L 37/26* (2013.01); *F16J 15/064* (2013.01); *A61M 39/18* (2013.01); *F16L 2201/44* (2013.01)

(58) Field of Classification Search
CPC .......... A61M 39/18; A61M 2039/1072; A61M 39/14; A61M 39/165; A61M 39/221; F16L 37/26; F16L 2201/44
See application file for complete search history.

(56) References Cited

U.S. PATENT DOCUMENTS

| | | | |
|---|---|---|---|
| 3,865,411 A | 2/1975 | Rowe et al. | |
| 3,909,910 A | 10/1975 | Rowe et al. | |
| 4,737,214 A | 4/1988 | Leurink et al. | |
| 5,492,147 A * | 2/1996 | Challender | A61M 39/26 604/905 |
| 6,883,778 B1 * | 4/2005 | Newton | A61M 39/26 604/905 |
| 6,976,494 B2 | 12/2005 | Wayne et al. | |
| 7,070,589 B2 | 7/2006 | Lolachi et al. | |
| 7,097,209 B2 | 8/2006 | Unger et al. | |

(Continued)

FOREIGN PATENT DOCUMENTS

| | | |
|---|---|---|
| CN | 108825884 | 11/2018 |
| DE | 32 10 964 | 10/1983 |

(Continued)

*Primary Examiner* — David Bochna
(74) *Attorney, Agent, or Firm* — Wenderoth, Lind & Ponack, L.L.P.

(57) ABSTRACT

A sterile connector includes a first section of tubing with a first end portion to be connected to a second end portion of a second section of tubing and/or another counterpart to establish fluid communication. An axial protrusion extends away from the first end portion of the first section of tubing in an axial direction, and a separation layer closes off an inside of the section of tubing. The separation layer has a predetermined breaking site, and the axial protrusion is connected pivotally to the first end portion of the first section of tubing to pivot from a first position to a second position when engaged with a second axial protrusion and/or with the other counterpart and is coupled to the separation layer to exert a breaking force on the separation layer in the second position.

19 Claims, 2 Drawing Sheets

(56) References Cited

U.S. PATENT DOCUMENTS

| | | | |
|---|---|---|---|
| 7,396,051 B2 * | 7/2008 | Baldwin | A61M 39/26 604/905 |
| 7,763,013 B2 | 7/2010 | Baldwin et al. | |
| 8,029,023 B2 | 10/2011 | Årthun et al. | |
| 8,454,579 B2 * | 6/2013 | Fangrow, Jr. | A61M 39/26 604/539 |
| 9,044,585 B2 | 6/2015 | Masuda et al. | |
| 9,186,493 B2 | 11/2015 | Pavlik | |
| 9,586,036 B2 | 3/2017 | Masuda et al. | |
| 10,111,809 B2 | 10/2018 | Pavlik | |
| 10,946,183 B2 | 3/2021 | Faldt et al. | |
| 10,952,769 B2 | 3/2021 | Suzuki et al. | |
| 11,713,840 B2 | 8/2023 | Gibson et al. | |
| 2001/0012930 A1 | 8/2001 | Ebner et al. | |
| 2002/0133136 A9 | 9/2002 | Lolachi et al. | |
| 2003/0060804 A1 * | 3/2003 | Vaillancourt | A61M 39/26 604/533 |
| 2004/0034328 A1 | 2/2004 | Unger et al. | |
| 2004/0079383 A1 | 4/2004 | Wayne et al. | |
| 2005/0015075 A1 * | 1/2005 | Wright | A61M 39/14 604/535 |
| 2005/0228362 A1 * | 10/2005 | Vaillancourt | A61M 39/26 604/533 |
| 2006/0157971 A1 | 7/2006 | Baldwin et al. | |
| 2008/0264450 A1 | 10/2008 | Baldwin et al. | |
| 2008/0277878 A1 | 11/2008 | Arthun et al. | |
| 2008/0306469 A1 | 12/2008 | Masuda et al. | |
| 2014/0155837 A1 | 6/2014 | Masuda et al. | |
| 2015/0061282 A1 | 3/2015 | Faldt et al. | |
| 2015/0157800 A1 * | 6/2015 | Chen | A61M 39/16 604/68 |
| 2015/0290448 A1 | 10/2015 | Pavlik | |
| 2016/0022538 A1 | 1/2016 | Pavlik | |
| 2017/0080203 A1 * | 3/2017 | Yeh | A61M 39/165 |
| 2017/0106182 A1 * | 4/2017 | Yoshioka | A61M 39/26 |
| 2017/0266429 A1 | 9/2017 | Striggow et al. | |
| 2017/0268709 A1 | 9/2017 | Gibson et al. | |
| 2017/0281921 A1 | 10/2017 | Faldt et al. | |
| 2019/0021951 A1 | 1/2019 | Pavlik | |
| 2019/0099593 A1 * | 4/2019 | Avula | A61M 39/165 |
| 2019/0175218 A1 | 6/2019 | Suzuki et al. | |
| 2019/0184152 A1 * | 6/2019 | Kakinoki | A61M 39/10 |
| 2020/0222681 A1 * | 7/2020 | Burkholz | A61M 39/26 |
| 2021/0162192 A1 | 6/2021 | Faldt et al. | |
| 2021/0262600 A1 | 8/2021 | Gibson et al. | |

FOREIGN PATENT DOCUMENTS

| | | |
|---|---|---|
| EP | 0 208 004 | 1/1987 |
| EP | 1 764 130 | 3/2007 |
| JP | 6-190055 | 7/1994 |
| WO | 2006/093450 | 9/2006 |
| WO | 2013/147688 | 10/2013 |
| WO | 2015/027277 | 3/2015 |
| WO | 2015/160522 | 10/2015 |

\* cited by examiner

STERILE CONNECTOR

BACKGROUND OF THE INVENTION

The present invention concerns a sterile connector for tubing, and a sterile connection between a section of tubing and a further section of tubing and/or another counterpart.

Accordingly, the invention concerns a sterile connector for tubing including a section of tubing with an end portion to be connected to a further end portion of a further section of tubing and/or to the other counterpart in order to establish fluid communication, at least one axial protrusion extending away from the end portion of the section of tubing in an axial direction of the section of tubing, and a separation layer which closes off an inside of the section of tubing.

Flexible tubing for medical and pharmaceutical (in particular, bio-pharmaceutical) use and connectors for the same are known in the prior art. Connectors for establishing fluid communication between two sections of tubing need to be configured such that the fluid communicating inside of both sections of tubing and the connector itself is sterile after the connection is complete.

In order to achieve this sterility, connectors of the prior art usually involve one or more separation layers, such as a film, which are pulled out from the outside in order to establish the fluid communication. Examples are disclosed in WO 2006/093450 A1 or WO 2013/147688 A1.

Another approach is disclosed in WO 2015/160522 A1 where a mechanical swivel-action is used for establishing the fluid communication.

Yet other approaches use various forms of welding or bonding in order to establish the fluid communication.

The sterile connections according to the prior art suffer from a high degree of complexity, both in terms of production and in terms of handling. Referring to the figures of the cited prior art document the intricate geometry disclosed is striking, which obviously results in difficult and costly production processes. Additionally, the connectors of the prior art involve a big number of separate parts, such as protective films, seals, and injection moulded parts.

In terms of handling the solutions according to the prior art all necessitate several steps for establishing the fluid communication, such as initially hooking up connector parts, pulling out separation layers, mechanical locking action, and the like.

SUMMARY OF THE INVENTION

The object of the invention is therefore to provide a sterile connector and a sterile connection which is simpler in terms of production and/or handling.

The sterile connector includes a separation layer having a predetermined breaking site. At least one axial protrusion is connected pivotally to the end portion of a (first) section of tubing to pivot from a first position to a second position when engaged with a further axial protrusion on the further end portion of the further (second) section of tubing and/or with another counterpart element, and is coupled to the separation layer so as to exert a breaking force on the separation layer in the second position which breaking force is big enough to break the separation layer at the predetermined breaking site.

Regarding the sterile connection, the (first) section of tubing and the further (second) section of tubing each comprise a sterile connector according to the invention, in which the respective axial protrusions are in the respective second positions and the respective separation layers are broken, preferably such that the respective end portions of the sections of tubing are in direct contact with each other.

It is a basic aspect of the invention to have the axial protrusion, which engages the further axial protrusion on the further section tubing or the other counterpart, exert a force on the separation layer big enough to break the separation layer at the predetermined breaking site. This makes it possible to establish the fluid communication in a single step, which is obviously a large step forward regarding the ease of use of a sterile connector compared to the prior art.

In the simplest embodiments, the invention can be realized with only a small number (two or three) of functional elements (axial protrusion, separation layer with predetermined breaking site) so that the invention can naturally be manufactured much easier than the sterile connectors of the prior art.

Another advantage of the invention is that the sterile connection according to the invention can be free of other parts or materials which come into contact with the fluid beside the sections of tubing connected to each other. Formulated differently, the sections of tubing which are brought into fluid communication with each other can be sealed against the environment by directly contacting facing surfaces of the sections of tubing, so that no other materials are in contact the fluid.

Especially in the medical and/or (bio-)pharmaceutical context, each material which comes into contact with the fluid communicated in the tubing has to undergo extensive testing in order to avoid harmful substances being released into the fluid by the material. Also in this way, the invention reduces the complexity of the sterile connector and sterile connection, as such tests simply do not have to take place.

In preferred embodiments, the breaking force exerted on the separation layer functions such that tensile load in the separation layer included by the breaking force causes the breaking of the predetermined breaking site.

The predetermined breaking site can, for example, be embodied as a thinning of the material of the separation layer. Such a thinning of the material can be substantial such that the thickness of the material at the predetermined breaking site of the separation layer only has a thickness of less than 10%, preferably less than 5%, and particularly approximately 1% compared to the thickness of the material at the rest of the separation layer. The thickness of the material at the predetermined breaking site can be chosen such that the break occurs at an exactly predetermined time during the tensioning of the separation layer during the connection process.

It is also conceivable to use a different material with a lower tensile strength than the rest of the separation layer for the predetermined breaking site.

Actual holes in the separation layer are not preferred as this may compromise the sterility of the inside of the section of tubing.

In the context of the invention, the at least one axial protrusion can be a single axial protrusion or there can be a plurality of axial protrusions. For the purposes of this document, the at least one axial protrusion is simply referred to as "axial protrusion", but it is always to be understood that there can be one or more axial protrusions, unless explicitly stated otherwise.

The tubing can in particular be flexible tubing so as to allow for bending and possibly kinking of the tubing.

The terms axial and radial are to be understood relative to a central axis of the section of tubing. The central axis does not necessarily have to be a straight line because the section of tubing can be bent or otherwise curved. The central axis can be understood as a "middle line" of the tubing, along which its fluid communication path extends.

The section of tubing and/or the separation layer can preferably be made of a transparent elastomer. Particularly preferably, the tubing can be made of a thermoplastic elastomer and/or preferably remain elastic (i.e. not brittle) over long periods of time.

Examples of materials for the section of tubing and/or the separation layer are EVA and/or PVC and/or any other flexible material suitable for tubing.

Preferably, the same material can be used for the section of tubing and the separation layer.

A protective cap can be present on the sterile connector in order to prevent damage and/or contamination. The protective cap can be removed immediately before making a connection according to the invention.

The sterile connection according to the invention can be made using two sterile connectors according to the invention. The two sterile connectors according to the invention can be embodied essentially in the same way or can be embodied differently, with the limitation that the respective axial protrusions, and sections of tubing, and possibly further elements need to be of compatible size. In principle, the further sterile connector, to which the sterile connector according to the invention is to be connected, i.e. the other counterpart, does not need to include a section of tubing, but can for example be part of a port on a machine or the like.

A clip, a hook, and/or a brace or the like can be provided in order to keep the sterile connector connected to the counterpart (the further sterile connector or the other counterpart).

In principle, the invention can be used to connect any types of tubing for any type of fluid, i.e. liquid or gas. Particularly preferred is the use for tubing communicating pharmaceutical, in particular biopharmaceutical, fluids.

The predetermined breaking site can be of point-like shape, and/or can be line-shaped, and/or cross-shaped. Preferred are embodiments with a single predetermined breaking site in the separation layer. Embodiments with more than one predetermined breaking site are conceivable however.

An elastic hinge can be provided for the pivotal connection of the axial protrusion to the end portion of the section of tubing. Elastic hinges are to be understood as hinges where the pivoting action is allowed by the flexibility/elasticity of the material of the hinge. Elastic hinges consequently do not require separately movable parts and therefore are very reliable. Additionally, since no separate parts are necessary, sealing of the hinge is not a problem.

In preferred embodiments, the axial protrusion is tensionless in the first position and/or tensioned in the second position. In other words, the first position is a relaxed position, while the axial protrusion (and consequently the separation layer) is under tension in the second position. In principle, other embodiments are conceivable where the first position is tensioned, e.g. with a pre-load.

Viewed in a longitudinal cross section, the axial protrusion can be connected to the end portion of the section of tubing through a U-shaped portion, wherein a first leg of the U-shaped portion is attached to the end portion of the section of tubing and a second leg of the U-shaped portion is attached to the axial protrusion. In particular, the U-shaped portion can be or form part of the flexible elastic hinge.

The U-shaped portion can be advantageous for transmitting a tension of the axial protrusion onto the separation layer, by forming three separate layers of material which have a greater bending stiffness than just one layer of material. This results in a greater breaking force (and optionally tensile load) being transmitted onto the separation layer.

Viewed in the longitudinal cross section, an opening of the U-shaped portion can face towards a central axis of the section of tubing and/or a closed side of the U-shaped portion can face outwards with respect to the section of tubing.

The section of tubing, the axial protrusion, and the separation layer can be made of the same material, wherein preferably the elastic hinge and/or the U-shaped portion is also made of the same material. This material may preferably be a flexible material.

The axial protrusion can be arranged circumferentially around the end portion of the section of tubing (in a view along the central axis of the section of tubing), preferably completely surrounding the end portion. Alternatively, there can be several axial protrusions, preferably distributed evenly around the end portion of the section of tubing.

Viewed in a longitudinal cross section, the axial protrusion can be provided with a surface facing away from the section of tubing in the axial direction. This surface can serve as engagement surface for engaging with a further axial protrusion or the like.

The axial protrusion can extend radially away from the section of tubing (besides extending away axially from the end portion of the section of tubing). Such a radial extending can allow for a larger engagement surface with the further sterile connector and/or other counterpart.

A connector element can be provided which surrounds the section of tubing, for example to improve grip for a person operating the sterile connector. The connector element can preferably be an injection moulded part.

The connector element can comprise a skirt configured to surround the end portion of the section of tubing and the axial protrusion when the section of tubing is connected to the further section of tubing and/or the other counterpart.

In some embodiments the skirt and the axial protrusion are sized such that the skirt is in contact with the axial protrusion when the axial protrusion is in the second position. This is however not necessary for the invention. A sufficient seal can also easily be achieved when there is no contact between the skirt and the axial protrusion.

The clip, hook, and/or brace or the like for keeping the connection according to the invention together can be arranged on the skirt.

The connector element can comprise a sheath portion which is in—preferably circumferential—contact with the section of tubing and which includes an edge portion configured to act as counter bearing against a base portion of the axial protrusion and/or the elastic hinge when the connector element is moved axially towards the end portion of the section of tubing. In other words, the edge portion can be used to pinch the base portion of the axial protrusion and/or the elastic hinge against a counterpart, such as a further axial protrusion. This increases the bending moment on the base portion of the axial protrusion, which in turn increases the tension transmitted onto the separation layer for easily breaking the predetermined breaking site.

BRIEF DESCRIPTION OF THE INVENTION

Further details and advantages are apparent from the figures and the accompanying description of the figures. The figures show:

DETAILED DESCRIPTION OF THE INVENTION

Figure 1:
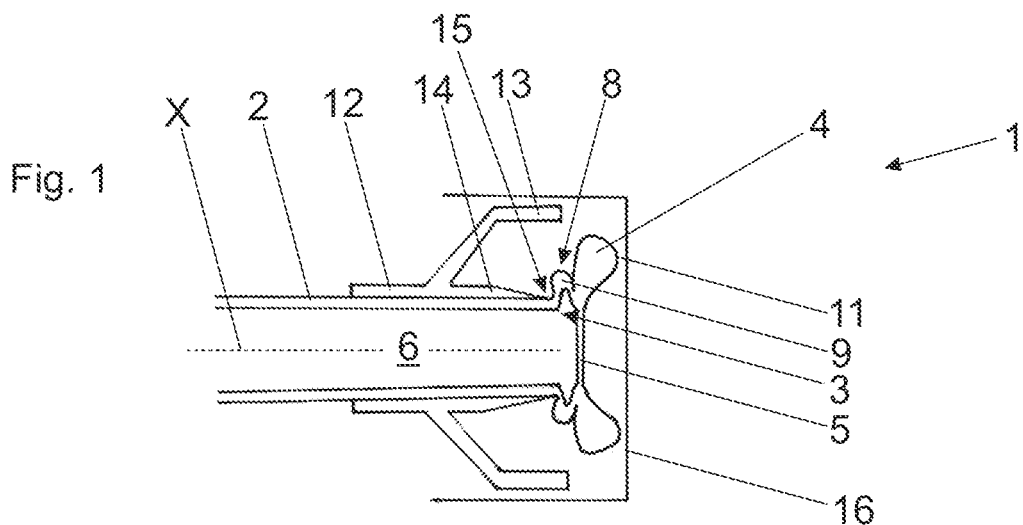
FIG. 1 shows a sterile connector according to the invention.

FIG. 1 shows the sterile connector 1 according to the invention. It includes a section of tubing 2, at the end of which there are provided an axial protrusion 4 and separation layer 5, which closes off the inside 6 of the section of tubing 2. The inside 6 is the area through which later fluid is conveyed. It extends along the central axis X of the section of tubing 2.

There is a U-shaped element 9 which connects the end portion 3 of the section of tubing 2 to the base of the axial protrusion 4, wherein a first leg of the U-shaped element 9 is attached to the end portion 3 of the section of tubing 2 and a second leg of the U-shaped element 9 is attached to the axial protrusion 4.

There is also a connector element 12 comprising a skirt 13 which surrounds the end portion 3 of the section of tubing 2 and the axial protrusion 4 when the section of tubing 2 is connected to the further section of tubing and/or the other counterpart.

The connector element furthermore comprises a sheath portion 14 with an edge portion 15.

The protective cap 16 can be removed immediately before establishing the sterile connection 11 according to the invention.

In order to keep the figures easily viewable only FIG. 1 has been furnished with all the reference numerals.

Figure 2:
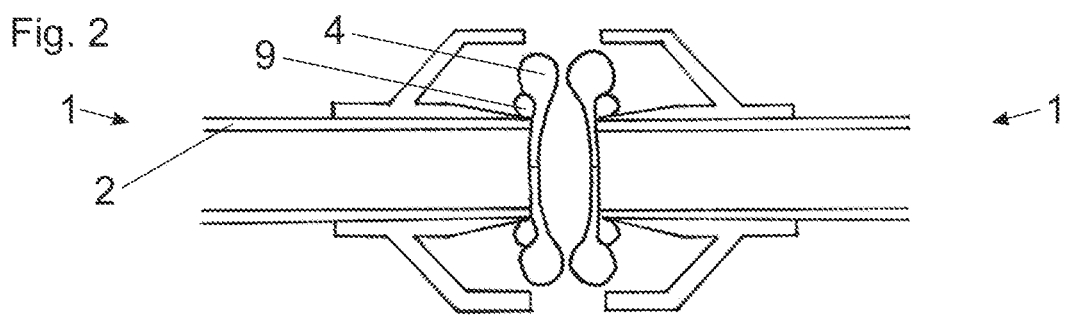
FIGS. 2 to 4 illustrates establishing the sterile connection according to the invention in three stages.
Figure 3:
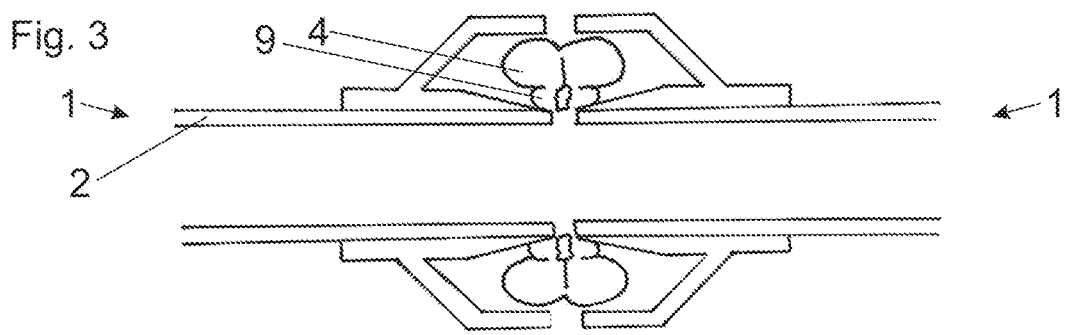
Figure 4:
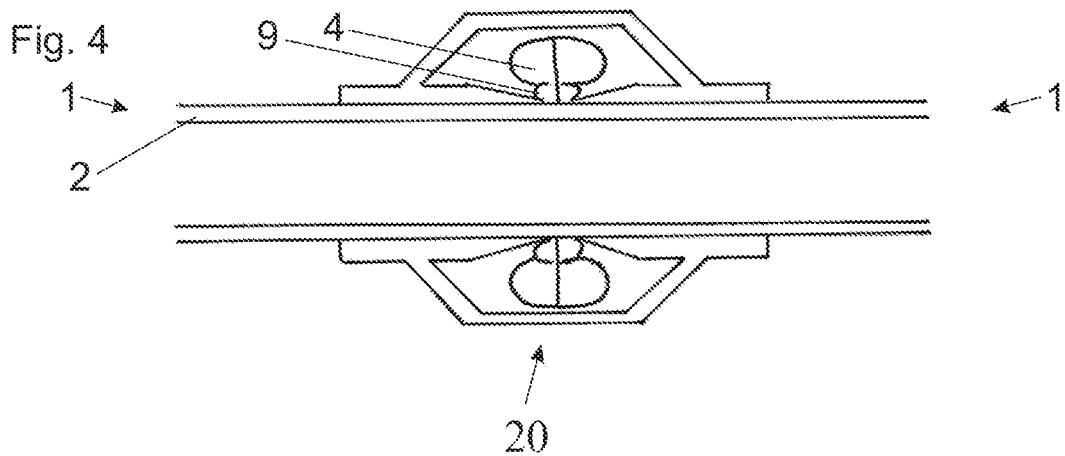

The function of the elastic hinge 8, the U-shaped element 9, the axial protrusion 4, and the edge portion 15 becomes apparent from FIGS. 2 to 4. In FIG. 1 the axial protrusion 4 is in the first position.

FIG. 2 shows the (first) sterile connector 1 according to the invention, with an equally embodied further (second) sterile connector 1 according to the invention where the respective axial protrusions 4 have just made contact with each other.

As can be seen the radially and axially extending axial protrusions 4 make for a relatively large engagement surface 11 such that the requirements for personnel aligning the sterile connectors are not too great.

As can also be seen in FIG. 2 the respective axial protrusions 4 have started to pivot backwards out of the first position towards the second position. Because of the stiffness of the material at the base of the axial protrusion 4 this tension is transferred as tensile load into the separation layer 5.

Persons skilled in the art will appreciate that the edge portion 15 and the U-shaped portion 9 contribute to an effective tensioning of the separation layer 5. When a person pushes the connector elements 12 towards each other, the edge portions 15 push into the first leg of the U-shaped portion 9. Because of the flexibility of the material from which the section of tubing 2, the U-shaped portion 9, and the axial protrusion 4 is made, the first leg of the U-shaped portion 9 is pressed onto the second leg of the U-shaped portion 9. Both press into the base of the axial protrusion 4.

As a result, the axial protrusion 4 is pivoted with the edge portion 15 as counter bearing towards the second position. Because of this pivoting action, the base of the axial protrusion 4 rotates (as a flexible elastic hinge 8 together with part of the U-shaped portion 9), and due to the stiffness of the material exerts a tensioning force onto the separation layer 5.

It should be mentioned, that the material of the tubing, even though it is flexible to a certain degree, has a large enough stiffness to transmit the tension into the separation layer 5. A special aspect of the embodiments shown in FIG. 1 and FIGS. 2 to 4 is that the stiffness/flexibility of the material of the tubing, the axial protrusion 4, and the U-shaped portion 9 is chosen such that the stiffness is small enough to allow for the pivoting action described above and at the same time large enough to transmit a large enough tension into the separation layer for breaking the predetermined breaking site.

In FIG. 3, this process has progressed so far that the predetermined breaking site has broken and the insides 6 of the respective sections of tubing 2 are now in fluid communication.

The second position is defined as the position of the axial protrusion 4 in which the tension of the separation layer 5 overwhelms the breaking resistance of the predetermined breaking site 7 (here in a position somewhere between FIGS. 2 and 3).

The person operating the sterile connectors 1 according to the invention then finishes the sterile connection 20 by bringing the connector elements 12 together completely.

Persons skilled in the art will appreciate that the edge portions 15 of the connector elements 12 support the seal between the sections of tubing 2 by pinching the respective U-shaped portions 9 and the bases of the respective axial protrusions 4 together.

In FIG. 4, the connection according the connection between the sterile connectors 1 is established.

A clip, hook, and/or brace or the like for keeping the sterile connector 1 according to the invention connected to the counterpart—in this case a further sterile connector 1—can preferably be arranged on the skirt 13. Such a clip, hook, and/or brace or the like can be embodied as in principle known in the prior art.

Figure 5:
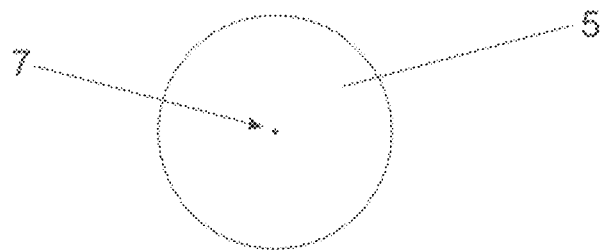
FIGS. 5 to 7 show three example configurations for predetermined breaking sites.
Figure 6:
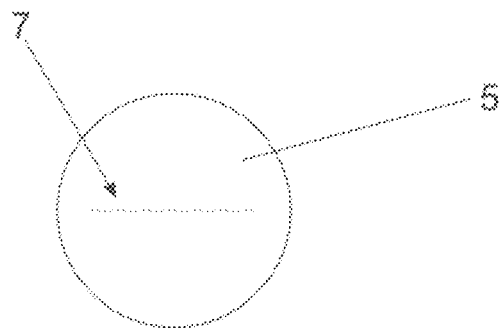
Figure 7:
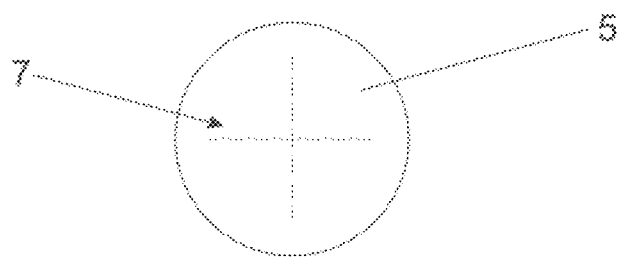

FIGS. 5, 6, and 7 show only the separation layer 5 in a view along the central axis X. Three different examples of predetermined breaking sites are shown, namely a point-like predetermined breaking site 7 in FIG. 5, a line-shaped predetermined breaking site 7 in FIG. 6, and a cross-shaped predetermined breaking site 7 in FIG. 7.

The invention does not only encompass embodiments with flexible hinges 8. For example mechanical hinges with a separation foil between the mechanical parts and the inside 6 are indeed conceivable.

The invention claimed is:

1. A sterile connection between a first section of tubing and a second section of tubing in fluid communication with each other, wherein the first section of tubing and the second section of tubing each comprise a sterile connector including:

a section of tubing with an end portion to be connected to a second end portion of a second section of tubing and/or a counterpart element to establish fluid communication, an axial protrusion extending away from the end portion of the section of tubing in an axial direction of the section of tubing, and a separation layer closing off an inside of the section of tubing, wherein the separation layer comprises a predetermined breaking site, and the axial protrusion:

is connected pivotally to the end portion of the section of tubing to pivot from a first position to a second position when engaged with a second axial protrusion on the second end portion of the second section of tubing and/or with the counterpart element, and is coupled to the separation layer so as to exert a breaking force on the separation layer in the second position which breaking force is big enough to break the separation layer at the predetermined breaking site; and wherein the respective axial protrusions are in respective second positions and the respective separation layers are broken.

2. The sterile connection according to claim 1, wherein the sterile connector of each of the first section of tubing and the second section of tubing further includes an elastic hinge for allowing the pivotal connection of the axial protrusion to the end portion of the section of tubing.

3. The sterile connection according to claim 2, wherein the elastic hinge is made of the same material as the section of tubing, the axial protrusion, and the separation layer.

4. The sterile connection according to claim 1, wherein the axial protrusion is tension-less in the first position and/or tensioned in the second position.

5. The sterile connection according to claim 1, wherein, when viewed in a longitudinal cross section, the axial protrusion is connected to the end portion of the section of tubing through a U-shaped portion, wherein a first leg of the U-shaped portion is attached to the end portion of the section of tubing and a second leg of the U-shaped portion is attached to the axial protrusion.

6. The sterile connection according to claim 5, wherein, when viewed in the longitudinal cross section, an opening of the U-shaped portion faces towards a central longitudinal axis of the section of tubing and/or a closed side of the U-shaped portion faces outwards with respect to the section of tubing.

7. The sterile connection according to claim 1, wherein the section of tubing, the axial protrusion, and the separation layer are made of the same material.

8. The sterile connection according to claim 1, wherein the axial protrusion is arranged circumferentially around the end portion of the section of tubing.

9. The sterile connection according to claim 8, wherein the axial protrusion completely surrounds the end portion of the section of tubing.

10. The sterile connection according to claim 1, wherein the axial protrusion extends radially away from the section of tubing.

11. The sterile connection according to claim 1, wherein, when viewed in a longitudinal cross section, the axial protrusion has a surface facing away from the section of tubing in the axial direction for engaging the second axial protrusion.

12. The sterile connection according to claim 1, wherein the sterile connector of each of the first section of tubing and the second section of tubing further includes a connector element surrounding the section of tubing.

13. The sterile connection according to claim 12, wherein the connector element comprises a skirt configured to surround the end portion of the section of tubing and the axial protrusion when the section of tubing is connected to the second section of tubing and/or the counterpart element.

14. The sterile connection according to claim 13, wherein the skirt and the axial protrusion are configured such that the skirt is in contact with the axial protrusion when the axial protrusion is in the second position.

15. The sterile connection according to claim 12, wherein the connector element comprises a sheath portion in contact with the section of tubing, the sheath portion including an edge portion configured to act as counter bearing against a base portion of the axial protrusion and/or an elastic hinge at a base of the axial protrusion when the connector element is moved axially towards the end portion of the section of tubing.

16. The sterile connection according to claim 15, wherein the sheath portion is in circumferential contact with the section of tubing.

17. The sterile connection according to claim 1, wherein the axial protrusion extends away from the section of tubing and away from the end portion of the section of tubing in the axial direction of the section of tubing.

18. The sterile connection according to claim 17, wherein the axial protrusion extends away from the section of tubing and away from the end portion of the section of tubing in a radial direction of the section of tubing.

19. The sterile connection according to claim 1, wherein the respective end portions of the sections of tubing are in direct contact with each other.

* * * * *